United States Patent [19]

Nishibori et al.

[11] Patent Number: 5,498,714

[45] Date of Patent: Mar. 12, 1996

[54] PROCESS FOR PRODUCTION OF TRIS (TRIBROMOPHENOXY)-S-TRIAZINE

[75] Inventors: Setsuo Nishibori, Shiga; Hideto Kondo, Kyoto, both of Japan

[73] Assignee: Dai-Ichi Kogyo Seiyaku Co., Ltd., Kyoto, Japan

[21] Appl. No.: 264,385

[22] Filed: Jun. 23, 1994

[30] Foreign Application Priority Data

| | | | |
|---|---|---|---|
| Jul. 8, 1993 | [JP] | Japan | 5-168833 |
| Jul. 9, 1993 | [JP] | Japan | 5-170285 |

[51] Int. Cl.⁶ .................. C07D 251/34
[52] U.S. Cl. ..................... 544/219
[58] Field of Search ................. 544/219

[56] References Cited

U.S. PATENT DOCUMENTS

| | | | |
|---|---|---|---|
| 3,682,908 | 8/1972 | Ismail | 544/219 |
| 3,843,650 | 10/1974 | Pews et al. | 260/248 |
| 4,039,538 | 8/1977 | Klinkenberg et al. | 544/219 |

FOREIGN PATENT DOCUMENTS

| | | |
|---|---|---|
| 1566675 | 5/1969 | France . |
| 47-25232 | 10/1972 | Japan . |
| 53-116390 | 10/1978 | Japan . |
| 3-34972 | 2/1991 | Japan . |
| 3034972 | 2/1991 | Japan . |

*Primary Examiner*—John M. Ford
*Attorney, Agent, or Firm*—Jordan and Hamburg

[57] ABSTRACT

This invention relates to a process for producing tris(tribromophenoxy)-s-triazine. This process is characterized by causing an aqueous tribromophenolate solution of not less than 50 weight % concentration containing a reducing agent to react on cyanuric chloride in the presence of a phase transfer catalyst. The process of this invention provides for a high output per unit reactor capacity. The yield and purity of the product are also high.

2 Claims, No Drawings

5,498,714

PROCESS FOR PRODUCTION OF TRIS (TRIBROMOPHENOXY)-S-TRIAZINE

FIELD OF THIS INVENTION

This invention relates to a process for producing tris(tribromophenoxy)-s-triazine.

Tris(tribromophenoxy)-s-triazine compounds as such are known from French Patent 1566675. It is also known from U.S. Pat. No. 3,843,650 and Japanese Kokai Patent Publication No. 47-25232 that these compounds have very satisfactory properties for application as flame retardants to synthetic resins. However, tris(tribromophenoxy)-s-triazine compounds as described in French Patent 1566675 were of low purity and could be made available only in low yield.

The technology for production of tris(tribromophenoxy)-s-triazine, thus far known from Japanese Kokai Patent Publication No. 47-25232 and U.S. Pat. No. 3,843,650, comprises dissolving cyanuric chloride in a ketone or cyclic ether solvent and adding an aqueous or ethanolic solution of a tribromophenolate. An alternative process, disclosed in JP Kokai No. 53-116390, comprises an alkali treatment in the presence of a phase transfer catalyst in a heterogeneous solvent system consisting of water and an organic solvent.

However, in the production system employing a hydrophilic solvent, solvent recovery entails the azeotropic inclusion of water in the recovered solvent and this water can hardly be removed from the solvent. If the recovered solvent is reused in the reaction, the charge cyanuric chloride is hydrolyzed and the resulting hydrolyzate contaminates the reaction system. This causes a decreased purity of the product compound and, when such product is added to synthetic resin, both the physical properties and flame resistance of the resin are adversely affected.

In the production system employing a non-hydrophilic solvent, as described in Japanese Kokai Patent Publication No. 3-34972, tris(tribromophenoxy)-s-triazine of high purity can be obtained in high yield but since the output per unit reactor capacity is as low as about 25%, this method is not satisfactory from economic points of view. Thus, a tribromophenolate can be easily synthesized by reacting tribromophenol with the corresponding alkali in water using the alkali in stoichiometric excess but when an aqueous tribromophemolate solution is prepared taking into consideration the productivity of tris(tribromophenoxy)-s-triazine, the workability of preparation of the tribromophenolate (the propensity of polymerization of tribromophenol) and the solubility of the tribromophenolate, its concentration cannot be higher than 48 weight %. However, when the concentration of the aqueous tribromophenolate solution is low, cyanuric chloride is hydrolyzed by water in its reaction with the tribromophenolate so that the product tris(tribromophenoxy)-s-triazine cannot be of high purity. Furthermore, a large quantity of a non-hydrophilic solvent is required to dissolve cyanuric chloride because of its low solubility and the output per reaction is necessarily low.

SUMMARY OF THE INVENTION

It is an object of this invention to provide a process for producing tris(tribromophenoxy)-s-triazine of high purity in high yield and with high productivity, i.e. high output per unit reactor capacity.

It is a further object of this invention to provide a process for preparing a stable, highly concentrated aqueous tribromophenolate solution which is virtually inhibited against polymer formation.

While contemplating on ways to reducing the amount of water in an aqueous solution of tribromophenolate, the inventors of this invention accidentally added a non-hydrophilic solvent for cyanuric chloride in the course of preparation of an aqueous tribromophenolate solution and found surprisingly that the tribromophenolate could be easily dissolved at a high concentration of not less than 50 weight %. The inventors further discovered that the output of tris(tribromophenoxy)-s-triazine per reaction could be increased by minimizing the hydrolysis of the charge cyanuric chloride through the decrease of water and dissolving the tribromophenolate at a high concentration.

This invention is, therefore, concerned with a process for producing tris(tribromophenoxy)-s-triazine which comprises causing an aqueous tribromophenolate solution of not less than 50 weight % concentration containing a reducing agent to act on cyanuric chloride in the presence of a phase transfer catalyst.

This invention is further concerned with a highly concentrated aqueous tribromophenolate solution containing a non-hydrophilic solvent and a reducing agent.

The invention is further directed to a method of preparing a highly concentrated aqueous tribromophenolate solution which comprises adding a non-hydrophilic solvent and a reducing agent in the preparation of said aqueous tribromophenolate solution from tribromophenol and an alkali.

In the context of this invention, the term highly concentrated aqueous tribromophenolate solution means an aqueous tribromophenolate solution of not less than 50% (weight %; the same applies hereinafter) concentration.

DETAILED DESCRIPTION OF THE PREFERRED EMBODIMENTS (1) Preparation of a tribromophenolate To prepare a tribromophenolate, an alkali, such as sodium hydroxide, potassium hydroxide or the like, and a reducing agent are dissolved in water, to begin with. To this aqueous solution, after cooling, is added a non-hydrophilic solvent. Then, tribromophenol is added and dissolved, either under heating or under stirring at room temperature. The preferred molar ratio of tribromophenol to alkali is 1:1–1.2. By adding a non-hydrophilic solvent in this manner, a highly concentrated aqueous tribromophenolate solution of not less than 50% can be prepared. Moreover, addition of such a non-hydrophilic solvent inhibits the oxidative polymerization of tribromophenol.

In this invention, the concentration of an aqueous tribromophenolate solution is the concentration in terms of tribromophenol. Thus, the concentration of tribromophenol relative to water can be calculated by the following equation.

$$\text{Concentration (\%)} = \frac{\text{Weight of tribromophenol}}{\text{Weight of tribromophenol + weight of water}} \times 100$$

Referring to workability, the preparation of a tribromophenolate can be facilitated by adding a non-hydrophilic solvent beforehand. Moreover, the aqueous tribromophenolate solution so prepared has a high specific gravity so that the aqueous layer separates readily from the non-hydrophilic solvent layer. The tribromophenolate is insoluble in the non-hydrophilic solvent. Therefore, by withdrawing the separated non-hydrophilic solvent and dissolving a fresh batch of tribromophenol therein, a large quantity of the tribromophenolate can be prepared even when the reactor is of limited capacity. The withdrawn non-hydrophilic solvent can be used as it is as the reaction solvent. In terms of productivity, too, since a large quantity of the tribromophenolate can be produced per unit reactor capacity, the output of tris(tribromophenoxy)-s-triazine per reaction can be increased. Furthermore, the amount of water finding its way into the reactor is so small that the hydrolysis of cyanuric chloride can be held at a minimum and the reaction can be conducted in dispersion, not requiring to completely dissolve cyanuric chloride in the non-hydrophilic solvent. In addition, when cyanuric chloride can be so handled, its powder can be directly added to the tribromophenolate solution for reaction.

The upper limit concentration of the aqueous tribromophenolate solution in this invention is 80%. The preferred concentration is 60–80%.

(2) Reducing agent

The reducing agent used in this invention functions to inhibit the oxidative polymerization of tribromophenol. Furthermore, when the reducing agent is used in conjunction with said non-hydrophilic solvent, the inhibitory effect on the oxidative polymerization of tribromophenol is further enhanced.

The reducing agent that can be used in this invention includes phenol compounds such as phenol, bromophenol, dibromophenol, 2,6-di-t-butyl-4-methylphenol (BHT), etc., sulfites such as ammonium sulfite, potassium sulfite, sodium sulfite, sodium hydrogensulfite, etc., and sulfides such as sodium sulfide, ammonium sulfide, potassium sulfide, etc., to name but a few. The level of addition of such reducing agent is 0.01–1.0 parts by weight to each 100 parts by weight of tribromophenol. If the level of addition is below 0.01 part by weight, the pot life of the aqueous tribromophenolate solution will be sacrificed by formation of red-brown polymers. If the level exceeds 1.0 part by weight, the reducing agent is not well soluble so that no appreciable effect of addition can be realized.

(3) Cyanuric chloride

For use in this invention, cyanuric chloride in the form of bulk powder can be directly subjected to the reaction. Alternatively, it can be dissolved or dispersed in the non-hydrophilic solvent before use.

(4) Solvent

The solvent for use in this invention is not critical in type only if it is non-hydrophilic. Thus, the solvent includes halogenated hydrocarbons such as methylene chloride, chloroform, carbon tetrachloride, trichloroethylene, perchloroethylene, tetrachloroethylene, etc., aromatic hydrocarbons such as benzene, toluene, xylene, etc., saturated hydrocarbons such as hexane etc., and halogen-substituted aromatic hydrocarbons such as chlorobenzene etc., among others. The preferred are solvents in which cyanuric chloride is well soluble, for example halogenated hydrocarbons such as chloroform and methylene chloride. For dissolving cyanuric chloride, two or more of these solvents can be used in combination. Moreover, the solvent for use in dissolving or dispersing cyanuric chloride may be different from the non-hydrophilic solvent for use in dissolving the tribromophenolate in water at a high concentration level. For dissolving the tribromophenolate, too, two or more non-hydrophilic solvents can be used in combination.

The solvent recovered by distillation can be reused as it is, or if necessary, the water contained can be removed with a dehydrating agent or the like. There is no particular limit to the amount of the solvent used for dissolving or dispersing cyanuric chloride but it is preferable to employ not less than 2.0 parts by weight of the solvent to each part by weight of cyanuric chloride. If the proportion of the solvent is less than the above limit, the reaction procedure may be interfered with. The non-hydrophilic solvent used for preparation of the tribromophenolate can be withdrawn from the top of the reactor after the preparation and, therefore, its amount is not restricted. However, it is preferably not less than 0.1 part by weight per part of tribromophenol. Below the above limit, preparation of the tribromophenolate is difficult. The preferred weight ratio of the non-hydrophilic solvent layer to the aqueous tribromophenolate solution layer after preparation of the solution is 1:5 through 1:2.

(5) Phase transfer catalyst

The phase transfer catalyst for use in this invention includes salts of quaternary phosphorus compounds such as triphenylbenzylphosphonium chloride, triphenylethylphosphonium bromide, butyltriphenylphosphonium chloride, phenacetyltriphenylphosphonium chloride, hexyltriphenylphosphonium bromide, octyltriphenylphosphonium bromide, tetraphenylphosphonium bromide, 2-methylbenzyltriphenylphosphonium bromide, methyltriphenylphosphonium iodide, phenacetyltriphenylphosphonium chloride, allyltriphenylphosphonium bromide, etc.; salts of quaternary nitrogen compounds such as tetramethylammonium chloride, tetramethylammonium bromide, tetraethylammonium chloride, tetraethylammonium bromide, tetrapropylammonium chloride, tetrapropylammonium bromide, tetrabutylammonium chloride, tetrabutylammonium bromide, trimethylphenylammonium chloride, trimethylphenylammonium bromide, triethylphenylammonium chloride, triethylphenylammonium bromide, trimethylbenzylammonium chloride, trimethylbenzylammonium bromide, triethylbenzylammonium chloride, triethylbenzylammonium bromide, tributylbenzylammonium chloride, tributylbenzylammonium bromide, dimethylbenzylphenylammonium chloride, dimethylbenzylphenylammonium bromide, tetrabenzylammonium chloride, tetrabenzylammonium bromide, tribenzylphenylammonium chloride, tribenzylphenylammonium bromide, trimethylcyclohexylammonium chloride, trimethylcyclohexylammonium bromide, tributylcyclohexylammonium chloride, tributylcyclohexylammonium bromide, trioctylmethylammonium chloride, trioctylmethylammonium bromide, trimethyl-n-laurylammonium chloride, trimethyl-n-laurylammonium bromide, n-laurylpyridinium chloride, n-laurylpyridinium bromide, n-stearylpyridinium chloride, n-stearylpyridinium bromide, etc.; crown ethers such as 15-crown-5, 18-crown-6, dibenzo-18-crown-6, dicyclohexyl-18-crown-6, dibenzo- 24-crown-8, dicyclohexyl-24-crown-8 and so on.

The level of addition based on cyanuric chloride is 0.1–10.0%, preferably 2.0–5.0%.

The phase transfer catalyst can be added to the tribromophenolate solution beforehand or to the cyanuric chloride solution.

(6) Production process

In the production process of this invention, a highly concentrated aqueous tribromophenolate solution of not less than 50% concentration is first prepared with the aid of a non-hydrophilic solvent and this solution is added dropwise to a solution (or suspension) of cyanuric chloride containing a phase transfer catalyst in a non-hydrophilic solvent or, alternatively, the phase transfer catalyst and powdery cyanuric chloride are added to the highly concentrated aqueous tribromophenolate solution. The preferred molar ratio of cyanuric chloride to tribromophenol is 1:2.94– 3.60. After the above dripping or addition, the reaction system is aged where necessary and the non-hydrophilic solvent is removed from the reaction system at atmospheric or subatmospheric pressure. In this manner, tris(tribromophenoxy)-s-triazine of high purity can be obtained.

The reaction temperature is not so critical but when the recovered solvent was used in dripping the aqueous tribromophenolate solution to a solution or dispersion of cyanuric chloride, the reaction system is preferably cooled to 10° C. or below up to immediately before the dripping of the aqueous tribromophenolate solution for suppressing the hydrolysis of cyanuric chloride. After the dripping has started, the reaction temperature may be increased up to the boiling point of the solvent. Preferably, however, the dropwise addition is carried out at a low temperature to minimize the hydrolysis of cyanuric chloride.

(7) Reaction mechanism

The phase transfer catalyst is a catalyst which can catalyze the reaction between the cyanuric chloride dissolved in a non-hydrophilic solvent and the tribromophenolate dissolved in water, i.e. in a heterogeneous solvent system consisting of water and a non-hydrophilic solvent. The reaction mechanism of this invention is that the phase transfer catalyst converts the water-soluble tribromophenolate to the oil-soluble tribromophenolate and the latter migrates into the non-hydrophilic solvent and reacts with cyanuric chloride there. After the reaction, the phase transfer catalyst is reused for the conversion of water-soluble tribromophenolate to oil-soluble tribromophenolate and the reaction is repeated.

(8) Additives

In this invention, various additives such as a stabilizer and an antifoam can be employed.

The production process of this invention for tris(tribromophenoxy)-s-triazine is superior to the prior art processes in productivity or output per unit reactor space, yield and product purity.

The highly concentrated aqueous tribromophenolate. solution according to this invention is highly stable and can be used in various reactions. According to the preparation method of this invention, a highly stable, highly concentrated aqueous tribromophenolate solution can be easily prepared.

The following examples are intended to illustrate this invention in further detail and should by no means be construed as defining the scope of the invention.

EXAMPLE 1

A 300 ml-capacity reactor equipped with a stirrer, condenser and thermometer was charged with water in the amount indicated in Table 1. Then, 6.1 g (0.15 mol) of sodium hydroxide and 0.05 g of sodium sulfite were added and dissolved. After the solution had cooled, 25 g of a non-hydrophilic solvent shown in Table 1 was added and, then, 50 g (0.15 mol) of 2,4,6-tribromophenol was added and dissolved. The solution was then cooled to a temperature not over 10° C.

The results of a visual inspection for the state of dissolution are shown in Table 1.

The concentration of TBP (2,4,6-tribromophenol) was calculated by means of the following equation.

$$\text{Concentration of } TBP\ (\%) = \frac{\text{Weight of } TBP\ (g)}{\text{Weight of } TBP\ (g) + \text{weight of water (g)}} \times 100$$

COMPARATIVE EXAMPLE 1

A 300 ml-capacity reactor equipped with a stirrer, condenser and thermometer was charged with water in an amount indicated in Table 1. Then, 6.1 g (0.15 mol) of sodium hydroxide and 0.05 g of sodium sulfite were added and dissolved. After the solution had cooled, 50 g (0.15 mol) of 2,4,6-tribromophenol was added and dissolved. The solution was then cooled to a temperature not over 10° C.

The results of a visual inspection for the state of dissolution is shown in Table 1.

TABLE 1

| | Non-hydrophilic solvent | Concentration of TBP (%)* | | | | | | |
|---|---|---|---|---|---|---|---|---|
| | | 45 (61) | 50 (50) | 55 (41) | 60 (33) | 65 (27) | 70 (21) | 75 (17) |
| Example 1 | Toluene | O | O | O | O | O | O | Δ |
| | Hexane | O | O | O | O | O | O | Δ |
| | Chlorobenzene | O | O | O | O | O | O | Δ |
| | Methylene chloride | O | O | O | O | O | O | O |
| Comparative Example 1 | — | O | Δ | X | X | X | X | X |

*: The figure in parentheses in the bottom line indicates the weight (g) of water.

Evaluation criteria o: Dissolved

Δ: Some of the crystals remained or crystals formed on cooling x: Not dissolved; the crystals remained.

EXAMPLE 2

A 300 ml-capacity reactor equipped with a stirrer, condenser and thermometer was charged with water in an amount indicated in Table 2. Then, 6.1 g (0.15 mol) of sodium hydroxide and 0.05 g of sodium sulfite were added and dissolved. After the solution had cooled, 25 g of methylene chloride was added and, then, 50 g (0.15 mol) of 2,4,6-tribromophenol was further added and dissolved. The solution was then cooled to a temperature not over 10° C. and the volume of the aqueous layer was measured. The results are shown in Table 2.

TABLE 2

| | | Concentration of TBP (%)* | | | | | | |
|---|---|---|---|---|---|---|---|---|
| | | 45 | 50 | 55 | 60 | 65 | 70 | 75 |
| TBP | (g) | 50 | 50 | 50 | 50 | 50 | 50 | 50 |
| Water | (g) | 61 | 50 | 41 | 33 | 27 | 21 | 17 |
| Sodium hydroxide | (g) | 6.1 | 6.1 | 6.1 | 6.1 | 6.1 | 6.1 | 6.1 |
| Sodium sulfite | (g) | 0.05 | 0.05 | 0.05 | 0.05 | 0.05 | 0.05 | 0.05 |
| Methylene chloride | (g) | 25 | 25 | 25 | 25 | 25 | 25 | 25 |
| Volume of aqueous layer | (ml) | 88 | 76 | 65 | 56 | 49 | 45 | 41 |

*: The concentration of TBP was determined in the same manner as described in Example 1.

EXAMPLE 3

A 300 ml-capacity reactor equipped with a stirrer, condenser and thermometer was charged with 27 g of water. Then, 6.1 g (0.15 mol) of sodium hydroxide and 0.05 g of sodium sulfite were added and dissolved. After the solution had cooled, 25 g of methylene chloride was added and, then, 50 g (0.15 mol) of 2,4,6-tribromophenol was further added and dissolved (TBP concentration, 65%). After dissolution, the stirring was stopped and the solution was visually examined for red-brown precipitates after 5, 10, 48, 72 and 120 hours.

The results are shown in Table 3.

COMPARATIVE EXAMPLE 2

A 300 ml-capacity reactor equipped with a stirrer, condenser and thermometer was charged with 27 g of water. Then, 6.1 g (0.15 mol) of sodium hydroxide was added and dissolved. After the solution had cooled, 25 g of methylene chloride was added and, then, 50 g (0.15 mol) of 2,4,6-tribromophenol was added and dissolved (TBP concentration, 65%). After dissolution, the stirring was stopped and the solution was visually examined for red-brown precipitates after 5, 10, 48, 72 and 120 hours.

The results are shown in Table 3.

COMPARATIVE EXAMPLE 3

A 300 ml-capacity reactor equipped with a stirrer, condenser and thermometer was charged with 65 g of water. Then, 6.1 g (0.15 mol) of sodium hydroxide was added and dissolved. After the solution had cooled, 50 g (0.15 mol) of 2,4,6-tribromophenol was added and dissolved (TBP concentration, 43%). After dissolution, the stirring was stopped and the solution was visually examined for red-brown precipitates after 5, 10, 48, 72 and 120 hours.

The results are shown in Table 3.

COMPARATIVE EXAMPLE 4

A 300 ml-capacity reactor equipped with a stirrer, condenser and thermometer was charged with 65 g of water. Then, 6.1 g (0.15 mol) of sodium hydroxide and 0.05 g of sodium sulfite were added and dissolved. After the solution had cooled, 50 g (0.15 mol) of 2,4,6-tribromophenol was added and dissolved (TBP concentration, 43%). After dissolution, the stirring was stopped and the solution was visually examined for red-brown precipitates after 5, 10, 48, 72 and 120 hours.

The results are shown in Table 3.

TABLE 3

|  |  | Time (Hr) | | | | |
| --- | --- | --- | --- | --- | --- | --- |
|  |  | 5 | 10 | 48 | 72 | 120 |
| Example | 3 | O | O | O | O | O |
| Comparative | 2 | O | O | Δ | X | X |
| Example | 3 | X | X | X | X | X |
|  | 4 | O | O | O | Δ | X |

Note)
O: Dissolved; no red-brown precipitates
Δ: Some red-brown precipitates
X: Red-brown precipitates all over

EXAMPLE 4

A 500 ml-capacity reactor equipped with a stirrer, condenser, thermometer and drip funnel was charged with 150 g of methylene chloride and 50 g (0.271 mol) of cyanuric chloride. After dissolution or dispersion, 1.6 g of triphenylethylphosphonium bromide was added.

Then, another 500 ml-capacity reactor equipped with a stirrer, condenser and thermometer was charged with 96 g of water. Then, 34.2 g (0.86 mol) of sodium hydroxide and 0.14 g of sodium sulfite were added and dissolved. After the solution had cooled to a temperature not over 10° C., 130 g of methylene chloride, i.e. the reaction solvent, was added. Then, 272 g (0.82 mol) of 2,4,6-tribromophenol was added and dissolved. The cooled tribromophenolate solution was added drop-wise to the above cyanuric chloride solution for reaction at a temperature of 3°–30° C. After completion of dropwise addition, the solution was aged under reflux for 3 hours. After aging, the methylene chloride was distilled off at atmospheric pressure.

The product was recovered by filtration and dried to provide white crystals of tris(tribromophenoxy)-s-triazine.

The results are shown in Table 4.

EXAMPLE 5

A 500 ml-capacity reactor equipped with a stirrer, condenser and thermometer was charged with 96 g of water. Then, 34.2 g (0.86 mol) of sodium hydroxide and 0.14 g of sodium sulfite were added and dissolved. After the solution had cooled to a temperature not over 10° C., 130 g of methylene chloride, i.e. the reaction solvent, was added. Then, 272 g (0.82 mol) of 2,4,6-tribromophenol was added and dissolved. After cooling, 1.6 g of triphenylethylphosphonium bromide and 150 g of methylene chloride were added. To the tribromophenolate solution thus prepared was added 50 g (0.271 mol) of cyanuric chloride powder at a reaction temperature of 3°–30° C. After completion of addition, the mixture was aged under reflux for 3 hours. After aging, the methylene chloride was distilled off at atmospheric pressure.

The product was recovered by filtration and dried to provide white crystals of tris(tribromophenoxy)-s-triazine.

The results are shown in Table 4.

COMPARATIVE EXAMPLE 5

A 500 ml-capacity reactor equipped with a stirrer, condenser, thermometer and drip funnel was charged with 160 g of methylene chloride and 25 g (0.136 mol) of cyanuric chloride. After dissolution or dispersion, 0.8 g of triethylbenzylammonium chloride was added.

Then, another 500 ml-capacity reactor equipped with a stirrer, condenser and thermometer was charged with 150 g of water. Then, 17.1 g (0.43 mol) of sodium hydroxide was added and dissolved. After the solution had cooled to a temperature not over 10° C., 136 g (0.41 mol) of 2,4,6-tribromophenol was added and dissolved. The cooled tribromophenolate solution was added dropwise to the above cyanuric chloride solution at a reaction temperature of 3°–30° C. After completion of dropwise addition, the solution was aged under reflux for 3 hours. After aging, the methylene chloride was distilled off at atmospheric pressure.

The product was recovered by filtration and dried to provide white crystals of tris(tribromophenoxy)-s-triazine.

The results are shown in Table 4.

TABLE 4

| | Example 4 | Example 5 | Comparative Example 5 |
|---|---|---|---|
| Concentration of TBP | 74 | 74 | 48 |
| Yield (g) | 278.2 | 278.3 | 136.2 |
| Yield (%) | 96 | 96 | 94 |
| Melting point (°C.) | 230.0 | 230.1 | 229.6 |
| Heat resistance (APHA)* | 70 | 70 | 100 |
| Output per unit reactor capacity (w/v %) | 55.6 | 55.6 | 27.2 |

*: A sample, 5 g, is taken in a Pyrex test tube, which is then placed in an aluminum block bath at a constant temperature of 300° C. and allowed to stand for 20 minutes. After cooling, methylene chloride is added to prepare a 2 w/v % solution. The color of the methylene chloride solution is measured against the APHA colorimetric tube (ASTM-D 1209).

What is claimed is:

1. A process for producing tris(tribromophenoxy)-s-triazine which comprises causing an aqueous tribromophenolate solution of not less than 50 weight % concentration containing a reducing agent to react on cyanuric chloride in the presence of a phase transfer catalyst.

2. The process according to claim 1 wherein said cyanuric chloride is subjected to reaction as dissolved or dispersed in a non-hydrophilic solvent.

* * * * *